Figure 1:
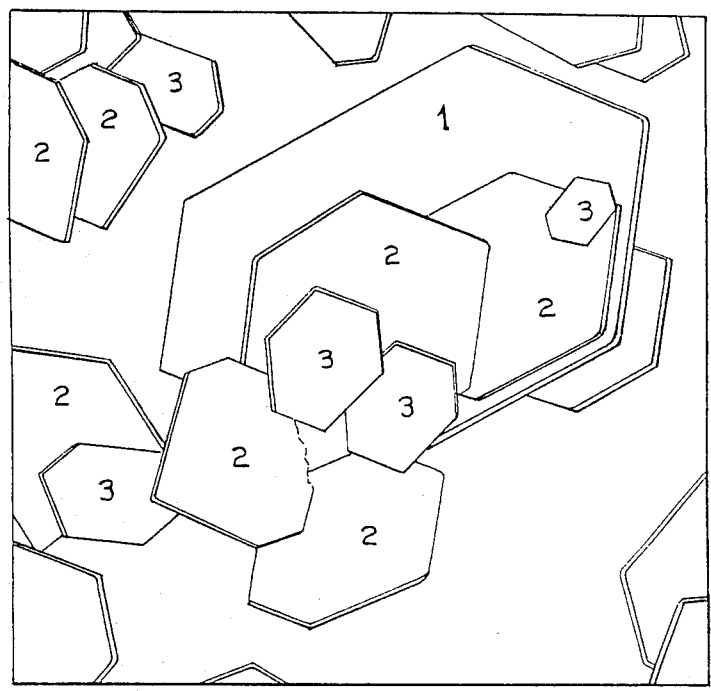

United States Patent [19]

Taylor et al.

[11] Patent Number: 4,544,761

[45] Date of Patent: Oct. 1, 1985

[54] PHARMACEUTICAL COMPOUND ZINC GLYCEROLATE COMPLEX PREPARED BY REACTING ZINC OXIDE AND GLYCEROL

[76] Inventors: Reginald M. Taylor, 48 Denning St., Hawthorn, State of South Australia 5062; Alan J. Brock, 26 Strangways Ter., North Adelaide, State of South Australia, both of Australia

[21] Appl. No.: 403,636

[22] PCT Filed: Nov. 18, 1981

[86] PCT No.: PCT/AU81/00164

§ 371 Date: Jul. 20, 1982

§ 102(e) Date: Jul. 20, 1982

[87] PCT Pub. No.: WO82/01867

PCT Pub. Date: Jun. 10, 1982

[51] Int. Cl.$^4$ ................................................ C01F 3/06
[52] U.S. Cl. .................................... 556/130; 514/494; 514/844
[58] Field of Search ...................... 260/429.9; 424/289

[56] References Cited

U.S. PATENT DOCUMENTS

| | | | |
|---|---|---|---|
| 2,595,371 | 5/1952 | Scanlan et al. | 424/289 X |
| 2,719,811 | 10/1955 | Cook et al. | 424/289 X |
| 3,859,236 | 1/1975 | Blewett et al. | 260/429.9 X |
| 3,996,346 | 12/1976 | Staffier | 424/67 |
| 4,160,821 | 7/1979 | Sipos | 424/289 X |
| 4,316,852 | 2/1982 | Blackford | 260/414 |

OTHER PUBLICATIONS

Taylor et al., Australian Journal of Chemistry, (1970), vol. 23, pp. 1963-1971.

*Primary Examiner*—Helen M. S. Sneed
*Attorney, Agent, or Firm*—Cushman, Darby & Cushman

[57] ABSTRACT

A pharmaceutical compound with therapeutic, prophylactic and cosmetic properties for human and veterinary use, being a zinc glycerolate complex formed as a reaction product of zinc oxide and glycerol having a platy morphology with generally hexagonal crystals (1/2/3) of relatively low thickness and high lubricity, with or without further reaction products or carriers.

24 Claims, 2 Drawing Figures

PHARMACEUTICAL COMPOUND ZINC GLYCEROLATE COMPLEX PREPARED BY REACTING ZINC OXIDE AND GLYCEROL

INTRODUCTION

This invention relates to certain pharmaceutical compounds and to their use for therapeutic and prophylactic treatment of the human body and for veterinary purposes.

More particularly the invention relates to use of metal glycerolate compounds as a base for the therapeutic and prophylactic treatment of certain skin disorders and irritations, and also for internal as well as external use. The use of the compounds also extends for use as a base for cosmetic preparations.

It is well known that at least several trace elements are required for cell division and tissue repair and for other bodily processes but there has always been the problem of finding a method of applying or supplying trace elements to the required point in a usable form and at the same time with negligible systemic toxicity.

In particular the metal zinc is necessary in trace element form for cell division and tissue repair and also in various compounds has a known slight bactericidal and fungicidal action on the skin and once again the problem is to apply the metal to the required site in a usable form.

Crystalline glycerato-metal complexes were first described in a paper in the Australian Journal of Chemistry volume 23, 1970, Page 1,963 and in that paper the method of forming these compounds and some of their physical properties are given. These compounds form during the heating of particular metal oxides, hydroxides or salts with glycerol at temperatures around 120° or higher.

The physical structure of the resulting chelated compounds generally produces a platy morphology resulting in a talc-like or slippery tactile impression.

BASIS OF THE INVENTION

The present applicant has found that the use of glycerato-metal complexes can be arranged to give valuable advantage in the treatment of various medical disorders, and extends to a method of treatment of skin disorders comprising the step of applying to the affected skin a modified zinc glycerolate complex including a pharmaceutically acceptable carrier or extender, or the compound may be used as a barrier substance or a sun screen or as a protective surface of high lubricity when applied to the skin.

According to the present invention advantageous properties of the zinc glycerolate complex are controlled during production to achieve a compound with the required characteristic, and the compound can be subsequently chemically altered by certain reagents to achieve a composition which may recommend its use because of specific effects in particular topical skin application whether for therapeutic or cosmetic purposes while maintaining the advantageous physical properties.

Any zinc salt or compound which decomposes to ZnO on heating at temperatures between approximately 120°–300° C. will form this compound. As an example of this further technique the heating of zinc acetate and glycerol forms a zinc glycerolate complex via a solution phase.

APPLICATION OF THE INVENTION

Research has shown that when zinc oxide is reacted with glycerol a reaction product results which either by itself or in combination with other substances is higly suitable as a pharmaceutical compound, particularly where high lubricity is required, the compound when examined by electron microscopy is shown to consist of crystals which can be of varying size which, by correct preparation, can range from large hexagonal crystals through a range of sizes to relatively small hexagonal crystals, the crystals according to the preferred formulation being in the nature of platlets of relatively low thickness and with low friction characteristics between the platlets so that the platlets slide readily one over the other to provide a thin but effective covering on a surface being treated. Because of the lubricity of the crystals they can move over each other freely to provide a required coverage, this being aided by the large variation in size of the relatively thin platlets so that smaller crystals fit into the spaces between larger crystals and provide a highly successful protective screen.

Figure 2:
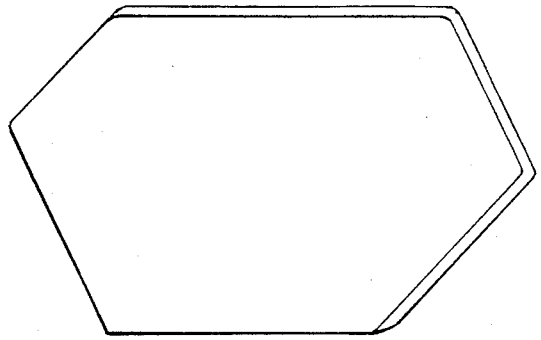

In the drawings:

FIG. 1 herein shows a drawing taken from a photograph of crystals of zinc glycerolate, using a magnification of 9000, and FIG. 2 shows one of the crystals, illustrating their plate-like nature, the photograph of that crystal having a magnification of 18,000.

FIG. 1 shows a large crystal 1 with medium sized crystals 2 and a range of sizes down to the smaller crystals 3, all however retaining their characteristic of elongated hexagonal configuration with relatively low thickness.

These crystals can be produced from either zinc oxide or zinc acetate when reacted with glycerol, but preferably zinc oxide is the medium used in that it produces the platlets illustrated, whereas the product formed by precipitation from the solution phase of zinc acetate in heated glycerol may exhibit additional particles the shape and size of which may detract from the overall lubricity.

The zinc glycerolate appears to conform to the general formulae $C_3H_6O_3Zn$ and the complex is most suitably formed from the high temperature heating with vigorous stirring of zinc oxide in glycerol.

During the reaction of glycerol to form $CH_2-O-Z_n$ type bonds, water is given off and must be removed or eliminated from the system. During this reaction the suspension becomes very viscous.

It has been found suitable to use 80 and 100 g fine colloidal zinc oxide in 1000 g glycerol, the excess glycerol being recovered after the basic complex has been formed.

Alternatively zinc acetate can be used as this dissolves in the hot glycerol and the precipitate formed is the desired product. However in both cases, vigorous stirring is needed to produce a small general particle size product with a preferable variation in crystal size and a talc-like, but non-greasy feel.

The mixture should be kept at about 260° C. for about 1 hour to ensure reaction has gone to completion.

The increased viscosity is noted in the temperature range 195°–220° C.

The material can be heated for longer than one hour at the maximum temperature if residual zinc oxide is still present.

Allow the suspension to cool to less than 50° C. then dilute with water and filter under suction. Wash with 96% ethanol and finally acetone and dry by air suction or in an oven at 50°-60° C.

On a commercial production scale the suspension, of the complex in the excess glycerol can be diluted with ethanol and this can be distilled off during the next process before further zinc oxide is added and the process repeated.

The theoretical zinc content on dried product is 42.06%.

SPECIFIC EXAMPLES

The following examples show applications of the invention.

EXAMPLE 1

A liter, 3-necked, round bottom flask equipped with a mechanical stirrer, a thermometer and an outlet for volatile bi-products was charged with glycerol (500 gms, 5.43 moles). The reaction vessel uas uniformly heated by an external mantle to 220° C. with stirring, zinc oxide (50 gms, 0.614 moles) was added at that temperature in small portions with vigorous stirring. Upon completion of addition the temperature was cautiously raised to 260° C. and vigorously stirred at that temperature for one hour. The reaction mixture was then allowed to cool to room temperature and the slurry poured into water (2 liters). The mixture was then filtered (Whatman No. 1 filter paper) through a Buchner funnel and the residue washed with alcohol (95%, 300 ml) and acetone (200 ml) then dried in a moderate oven (60°) for four hours. A white, finely divided colourless odourless solid with a characteristic slippery feel was obtained. The particle size varied from 10-20 microns, consisting of platy crystals with hexagonal morphology. The yield was 86 gms or 90% (theoretical yield: 95.45 gms). The I.R. was identical to literature values. Assay Zn content actual=43.56% (theoretical 42.06%).

EXAMPLE 2

Glycerol (500 g, 5.43 moles) was placed in a large beaker into which a thermometer and a heavy duty mechanical stirrer were suspended. The stirring blade was designed so that it swept just above the base of the beaker providing very efficient mixing.

The glycerol was heated to 120° C. with stirring. Zinc oxide (50 g, 0.614 moles) was added at this temperature to form a well dispersed suspension. The mixture was then slowly heated with vigorous stirring to 260° C. During the heating process, two changes in viscosity were noted. The first was a thickening of the reaction mixture to an almost paste consistency, then upon further heating the reaction mixture became less viscous.

The reaction mixture was heated with vigorous stirring at 260° C. for one hour, allowed to cool to room temperature then poured into water (3 liters) and filtered through a Buchner funnel. The residue was suspended to ethanol, filtered, washed with acetone and dried in a moderate oven. The yield was 89 g or 93% (theoretical yield=95.45 g).

The crystals produced by this method consisted of a mixture of small hexagonal plates (~10 microns) and elongated crystals.

EXAMPLE 3

As per Example 1 except zinc acetate (50 gms, 0.23 moles) was used instead of zinc oxide. The product zinc glycerolate was isolated as above in 85% yield. The particle size varied from 10-70 microns, while the crystals were a mixture of elongated filament clusters and platlet structures.

EXAMPLE 4

As per Example 2 except zinc acetate (50 gms, 0.23 moles) was added to the glycerol before the reaction was heated. The reaction mixture was then heated to 260° C., vigorously stirred at this temperature for one hour, then worked up as described in Example 1. Yield=85%. The particle size varied from 10-100 microns while the crystals were a mixture of elongated filaments and platlet structures.

In carrying out the process it was found that the reacton of zinc oxide with glycerol proceeded slowly below 210° C. but very rapidly at 220° C. A ratio 1:10 zinc oxide to glycerol while not the only ratio possible was found the most convenient.

The high insolubility of zinc glycerolate in water and organic solvents means that crystals cannot be obtained by growth from solution.

However the unique properties of zinc glycerolate are related in part to its small but varying crystal size and crystal shape, the product produced by the reaction of zinc acetate and glycerol producing larger crystals than the reaction of zinc oxide with the latter.

To suit varying conditions of therapeutic or prophylactic treatments, other substances can be added as an admixture or as a means of producing further reaction products, and for example an aqueous solution of a copper salt may be added to the zinc glycerolate to replace small amounts of zinc in the complex by copper, resulting in a colour change and the ability to bring trace amounts of copper into contact with the skin when used as an ointment.

EXAMPLE 5

A weak neutral solution of cupric chloride was shaken with a little zinc glycerolate, the mixture was filtered through a Buchner funnel and the residue washed in turn with alcohol and acetone. The product so formed was blue in colour.

A further example may be given by the chemical absorption of suitable dyes by the zinc glycerolate giving a resultant obvious or non-obvious coloration when applied to the skin without destruction of the lubricity, or tactile qualities that make the original zinc compound advantageous for particular applications.

EXAMPLE 6

Zinc glycerolate which was tan in colour was obtained by the addition of certolake erythrosine (0.1 g) and certolake tartrazine (0.4 g) to zinc oxide (40 g) prior to reaction with glycerol in the manner described in Example 1.

The use of the zinc glycerolate as a topical application is not limited to its combination with metal cations or dye-stuffs given in the examples above but embraces all complexes with specific reactions for skin disorders or all complexes preferred for use in cosmetic applications as may react and bond with the zinc glycerolate while not destroying its essential structure and desirable characteristics.

The applicants have further found that the zinc glycerolate (II) complex has been found to provide a novel and efficient cream for shaving when it incorporates oils or soaps.

EXAMPLE 7

Shaving Cream

Mix together the following and heat to 60° C. (A)

| | |
|---|---|
| Glycerol monostearate | 10 g |
| Paraffin oil | 3 g |
| Lanolin | 5 g |
| Glycerol | 3 g |
| Stearic Acid | 2 g |

Mix together potassium hydroxide and water in the following proportions and heat to 60° C. (B)

| | |
|---|---|
| Potassium hydroxide | 0.1 g |
| Water | 71.9 g |

Mix (A) and (B) and stir to 45° C., add zinc glycerolate, 5 g and stir to room temperature.

Because of its covering power and adhesion on skin surfaces and its heavy metal content it may reduce the transmission of ultra-violet radiation in certain wavelength bands and thus it is believed that the compounds could reduce the effects of various skin disorders arising out of exposure to sunlight, while presenting properties of a non-apparent topical application.

EXAMPLE 8

Sunscreen

Mix together the following and heat till melted (A)

| | |
|---|---|
| Oleic Acid | 0.5 g |
| Peanut oil | 21.5 g |
| Lanolin | 17.5 g |

Add zinc glycerolate 32 g and stir and add calcium hydroxide solution B.P., 28.5 g gradually, continue stirring till thick cream is produced.

For the applications embraced by this invention an advantage is gained when these compounds and in particular the zinc glycerolate are formed with a pronounced hexagonal plate morphology with particle sizes as measured by the diameter of the platy particles being greater than six micro meters. This morphology and particle size adds to the coverage on and the easier application to skin surfaces. However the invention embraces the use of these compounds for the purposes described regardless of particle size and morphology. This platy morphology would reduce the tendency towards irritation to the respiratory system sometimes produced by the inhalation of acicular shaped fine powdery substances.

The benefits of these compounds and in particular the zinc glycerolate for the applications embraced by this invention arise from this platy morphology of the particles, their skin covering power and adhesion, their relative insolubility in water and common organic solvents, the exhibition of a hydrophobic character which appears to allow skin moisture to be retained, and its apparent ability to reduce the action of fungi, moulds and bacteria, a property exhibited by several organic and inorganic zinc salts.

The zinc glycerolate complex has been found to be effective in the treatment and prevention of ammoniacal dermatitis (burns in the genital areas of babies which originate from ammonia liberated during the decomposition of urine-nappy rash), in the treatment of pruritus, especially in people confined to bed or immobility, for the alleviation of psoriasis, for the treatment and prevention of fungal or bacteriacidal decomposition of tissue and the resultant odours arising in such complaints as tinea pedis and for the prevention of industrial dermatitis arising from particular environments. It is also envisaged that the properties of this compound would make it effective in the treatment of ichthyosis.

This invention is not restricted to the use of zinc glycerolate in only the above therapeutic and prophylactic applications but it embraces all other use of this compound when reacted or blended with other therapeutic substances.

The claims defining the invention are as follows:

1. A pharmaceutical compound formed by the process of reacting zinc oxide with glycerol by raising the temperature to about 260° C. and maintaining the temperature until reaction is completed to form $C_3H_6O_3Zn$, cooling the reaction mixture and pouring the zinc glycerolate slurry so formed into water, adding copper to the said slurry and shaking to cause zinc to be replaced by the said copper, and filtering the residue and washing and drying to produce a modified zinc glycerolate complex.

2. The pharmaceutical compound according to claim 1 wherein the copper is added as an aqueous solution of a copper salt.

3. A composition formed by the process of reacting zinc oxide with glycerol by raising the temperature to about 260° C. and, maintaining the temperature until reaction is complete to form $C_3H_6O_3Zn$, cooling the reaction mixture and pouring the slurry so formed into water, filtering, washing and drying to isolate zinc glycerolate, and blending into the zinc glycerolate and oleaginous substance for application of the blend to the skin as a therapeutic or prophylactic or cosmetic substance.

4. A composition according to claim 3 wherein the oleaginous substance is a mixture of glycerol monostearate, paraffin oil, lanolin, glycerol and stearic acid to produce a shaving cream, the mixture being further mixed with potassium hydroxide and water and blended with the zinc glycerolate complex.

5. A composition according to claim 3 wherein the oleaginous substance is oleic acid, peanut oil and lanolin mixed together and melted and applied to the zinc glycerolate while blending in calcium hydroxide solution to form a sun screen.

6. A pharmaceutical which is a mixture of a zinc glycerolate complex having the formula $C_3H_6O_3Zn$ formed as a reaction product of zinc oxide and glycerol at a temperature range between 120° and 300° C., having a platy morphology with generally hexagonal crystals of relatively low thickness and high lubricity and an oleaginous substance suitable for application to the skin as a therapeutic or prophylactic or cosmetic substance.

7. A pharamceutical according to claim 6 wherein the oleaginous substance is a mixture of glycerol monostearate, paraffin oil, lanolin, glycerol and stearic acid to produce a shaving cream, the mixture being further mixed with potassium hydroxide and water and blended with the zinc glycerolate complex.

8. A pharmaceutical according to claim 6 wherein the oleaginous substance is oleic acid, peanut oil and lanolin mixed together and melted and applied to the zinc glycerolate while blending in calcium hydroxide solution to form a sun screen.

9. A method of applying a therapeutic or prophylactic or cosmetic material to the skin comprising applying to the skin a zinc glycerolate complex having the formula $C_3H_6O_3Zn$ formed as a reaction product of zinc oxide and glycerol at a temperature range between 120° and 300° C., having a platy morphology with generally hexagonal crystals of relatively low thickness and high lubricity.

10. A method according to claim 9 wherein the zinc glycerolate complex is formed by the process of reacting zinc oxide or zinc acetate with glycerol in the proportions of about 50 gms zinc oxide or zinc acetate to 500 gms glycerol, raising the temperature of the mix to about 260° C. and maintaining the temperature until reaction is completed, cooling and pouring the mixture so formed into water, filtering, washing and drying to isolate the zinc glycerolate complex.

11. A method of applying a therapeutic or prophylactic or cosmetic material to the skin comprising applying to the skin the composition of claim 1.

12. A method of applying a therapeutic or prophylactic or cosmetic material to the skin comprising applying to the skin a composition formed by the process of reacting zinc oxide with glycerol wherein a colouring dye is added to the zinc oxide before forming an admixture with the glycerol, raising the temperature of the mixture to about 260° C. and maintaining the temperature until reaction is completed to form $C_3H_6O_3Zn$, cooling the reaction mixture and pouring the slurry so formed into water, filtering the residue and washing and drying to produce the coloured zinc glycerolate complex.

13. A method according to claim 12 wherein the dye is a mixture of certolake erythrosine and certolake tartrazine to produce a tan coloured zinc glycerolate.

14. A method of applying a therapeutic or prophylactic or cosmetic material to the skin comprising applying to the skin the composition of claim 3.

15. A method according to claim 14 wherein the oleaginous substance is a mixture of glycerol monostearate, paraffin oil, lanolin, glyercol and stearic acid the mixture being further mixed with potassium hydroxide and water and blended with the zinc glycerolate complex to form a shaving cream.

16. A method according to claim 14 wherein the oleaginous substance is oleic acid, peanut oil and lanolin mixed together and melted and applied to the zinc glycerolate while blending in calcium hydroxide solution to form a sun screen.

17. A method of applying a therapeutic or prophylactic or cosmetic material to the skin comprising applying to the skin the composition of claim 6.

18. A method of applying a therapeutic or prophylactic or cosmetic material to the skin comprising applying to the skin the composition of claim 7.

19. A method of applying a therapeutic or prophylactic or cosmetic material to the skin comprising applying to the skin the composition of claim 8.

20. A compound according to claim 1 wherein the complex is prepared by reacting 80 to 100 parts by weight of zinc oxide or zinc acetate to 100 parts by weight of glycerol.

21. A composition formed by the process of reacting zinc oxide or zinc acetate with glycerol wherein a colouring dye is added to the zinc oxide or zinc acetate before forming an admixture with the glycerol, raising the temperature of the mixture to about 260° C. and maintaining the temperature until reaction is completed to form $C_3H_6O_3Zn$, cooling the reaction mixture and pouring the slurry so formed into water, filtering the residue and washing and drying to produce the coloured zinc glycerolate complex there being employed 80 to 100 parts by weight of zinc oxide or zinc acetate to 1000 parts by weight of glycerol to the form the complex.

22. A composition according to claim 3 wherein the complex is prepared by reacting 80 to 100 parts by weight of zinc oxide or zinc acetate to 1000 parts by weight of glycerol.

23. A composition according to claim 6 wherein the complex is prepared by reacting 80 to 100 parts by weight of zinc oxide or zinc acetate to 1000 parts by weight of glycerol.

24. A method according to claim 9 wherein the complex is formed by reacting 80 to 100 parts by weight of zinc oxide or zinc acetate to 1000 parts by weight of glycerol.

* * * * *